US009107718B2

(12) United States Patent
Isch

(10) Patent No.: US 9,107,718 B2
(45) Date of Patent: Aug. 18, 2015

(54) BONE PLATE

(75) Inventor: Bryce A. Isch, Bluffton, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 52 days.

(21) Appl. No.: 13/347,410

(22) Filed: Jan. 10, 2012

(65) Prior Publication Data

US 2013/0178902 A1 Jul. 11, 2013

(51) Int. Cl.
*A61B 17/80* (2006.01)
*A61B 17/00* (2006.01)

(52) U.S. Cl.
CPC ............ *A61B 17/8085* (2013.01); *A61B 17/80* (2013.01); *A61B 2017/00526* (2013.01); *Y10T 156/1043* (2015.01)

(58) Field of Classification Search
CPC ............... A61B 17/70; A61B 17/8028; A61B 17/8052; A61B 17/8057; A61B 17/8085
USPC .............. 606/70, 71, 280–286, 298, 299, 291
See application file for complete search history.

(56) References Cited

U.S. PATENT DOCUMENTS

| 7,806,911 | B2 * | 10/2010 | Peckham ...................... 606/248 |
| 2006/0247638 | A1 * | 11/2006 | Trieu et al. ...................... 606/69 |
| 2010/0082069 | A1 | 4/2010 | Wolter | |
| 2012/0071875 | A1 * | 3/2012 | Von Wieding et al. ......... 606/71 |

FOREIGN PATENT DOCUMENTS

| WO | WO 2007/109431 A2 | 9/2007 |
| WO | WO 2007/109431 A3 | 9/2007 |
| WO | PCT/US2012/055197 | 2/2013 |
| WO | PCT/US2012/055197 | 4/2013 |

OTHER PUBLICATIONS

Int'l. Prelim. Report on Patentability and Written Opinion of the International Searching Authority for PCT Application No. PCT/US2012/055197, Jul. 15, 2014 (10 pages).

* cited by examiner

*Primary Examiner* — Ellen C Hammond
*Assistant Examiner* — Christina Negrellirodrigue
(74) *Attorney, Agent, or Firm* — Taft Stettinius & Hollister LLP; Ryan O. White

(57) ABSTRACT

A composite bone plate comprising: (a) a rigid ring that defines an internal opening and the outline of a bone plate; and, (b) a deformable material mounted to the rigid ring and at least partially spanning the internal opening, the deformable material including at least one through opening that is concurrently circumscribed by the rigid ring.

15 Claims, 2 Drawing Sheets

BONE PLATE

RELATED ART

Field of the Invention

The present invention is directed to implantable bone plates and, more specifically, to implantable bone plates that include deformable material through which one or more fasteners may extend to mount the bone plate to bone.

INTRODUCTION TO THE INVENTION

It is a first aspect of the present invention to provide a composite bone plate comprising: (a) a rigid ring that defines an internal opening and the outline of a bone plate, and (b) a deformable material mounted to the rigid ring and at least partially spanning the internal opening, the deformable material including at least one through opening that is concurrently circumscribed by the rigid ring.

In a more detailed embodiment of the first aspect, the deformable material comprises polyether ether ketone in a bone plate shape. In yet another more detailed embodiment, the deformable material is in the shape of a volar bone plate. In a further detailed embodiment, the deformable material comprises a higher volume percentage of the composite bone plate than does the rigid ring, and the deformable material comprises a lower weight percentage of the composite bone plate than does the rigid ring. In still a further detailed embodiment, the rigid ring comprises a metal and the rigid ring is in the shape of a volar bone plate. In a more detailed embodiment, the rigid ring comprises a metal and the rigid ring is in the shape of a spinal bone plate. In a more detailed embodiment, the rigid ring is concave on an inner circumferential surface, the deformable material is convex on an outer circumferential surface, and the inner circumferential surface contacts at least a portion of the outer circumferential surface. In another more detailed embodiment, the deformable material is concave on an outer circumferential surface, the rigid ring is convex on an inner circumferential surface, and the inner circumferential surface contacts at least a portion of the outer circumferential surface. In yet another more detailed embodiment, the deformable material includes a plurality of through openings, at least one of the plurality of through openings having a non-uniform circular vertical cross-section.

It is a second aspect of the present invention to provide a method of fabricating a bone plate comprising: (a) fabricating a deformable material into the shape of a bone plate, the deformable material including a plurality of through holes; (b) fabricating a rigid ring having an outline that tracks an outline of the deformable material; and, (c) mounting the deformable material to the rigid ring.

In a more detailed embodiment of the second aspect, the step of fabricating the deformable material includes shaping the deformable material into the shape of a volar bone plate. In yet another more detailed embodiment, the deformable material comprises polyether ether ketone. In a further detailed embodiment, the deformable material is fabricated in the shape of a volar bone plate. In still a further detailed embodiment, the step of mounting the deformable material to the rigid ring includes at least one of compressing an outer circumferential surface of the deformable material and expanding an inner circumferential surface of the rigid ring.

It is a third aspect of the present invention to provide a variable angle bone plate comprising: (a) a rigid frame; and, (b) a deformable material mounted to the rigid frame to create a bone plate, the bone plate having a plurality of holes extending through the deformable material, at least a first of the plurality of holes having a through axis that is not coaxial with a second of the plurality of through holes, wherein the bounds of the plurality of through holes are deformable without deforming the rigid frame.

In a more detailed embodiment of the third aspect, the deformable material comprises a higher volume percentage of the variable angle bone plate than does the rigid frame, and the deformable material comprises a lower weight percentage of the variable angle bone plate than does the rigid frame. In yet another more detailed embodiment, the rigid ring comprises a metal and the deformable material comprises polyether ether ketone. In a further detailed embodiment, at least one of the plurality of holes has a non-uniform circular vertical cross-section. In still a further detailed embodiment, the rigid frame is concave on an inner circumferential surface, the deformable material is convex on an outer circumferential surface, and the inner circumferential surface contacts at least a portion of the outer circumferential surface. In a more detailed embodiment, the deformable material is concave on an outer circumferential surface, the rigid frame is convex on an inner circumferential surface, and the inner circumferential surface contacts at least a portion of the outer circumferential surface.

DETAILED DESCRIPTION

The exemplary embodiments of the present invention are described and illustrated below to encompass implantable bone plates that include deformable material through which one or more fasteners may extend to mount the bone plate to bone. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention. It should also be noted that use of "or" as part of the instant disclosure should be construed to include the alternative and in conjunction.

Figure 1:
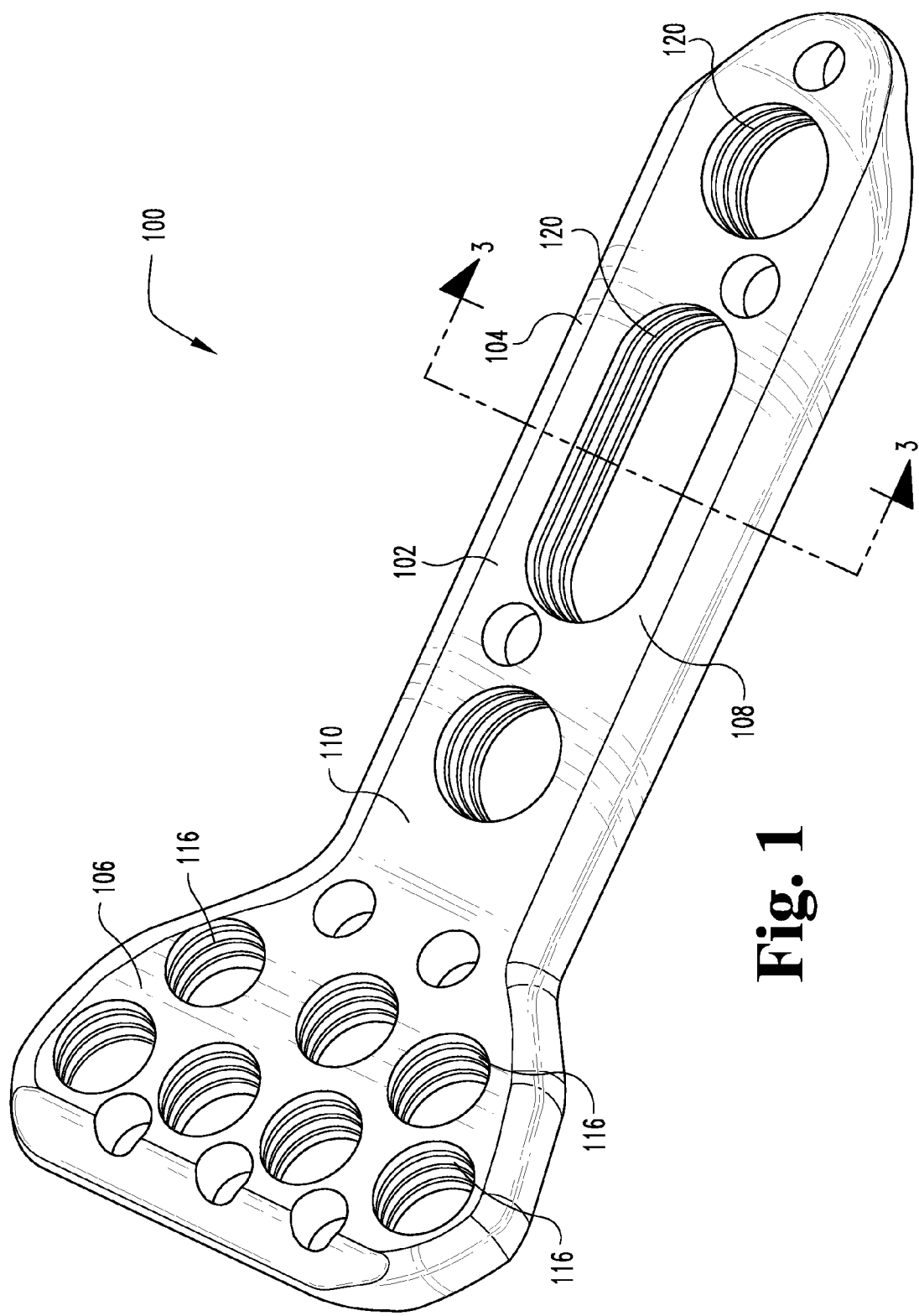
FIG. 1 is an overhead view of a first exemplary composite bone plate in accordance with the instant disclosure.
Figure 2:
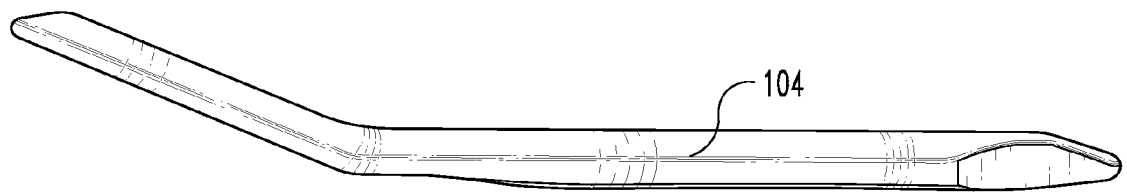
FIG. 2 is a profile view of the deformable insert of the composite bone plate of FIG. 1.
Figure 3:
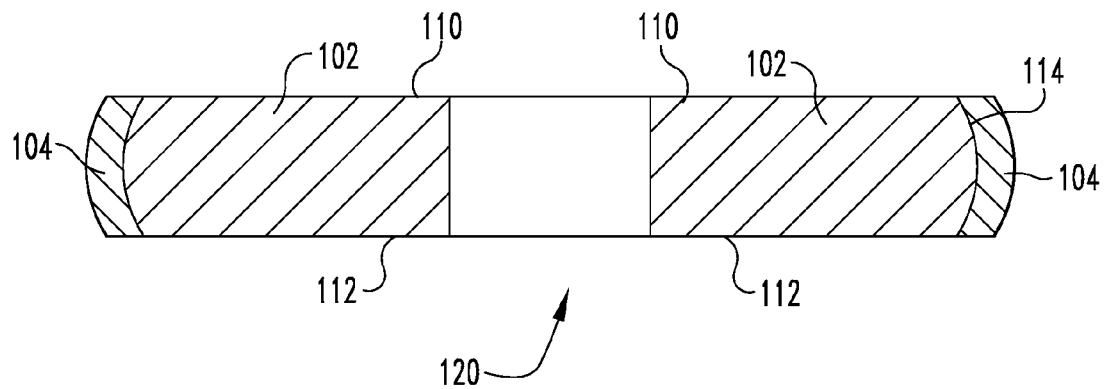
FIG. 3 is a cross-sectional view of the exemplary composite bone plate of FIG. 1 taken along line 3-3.

Referencing FIGS. 1-3, a first exemplary bone plate 100 includes a non-metallic substrate 102 surrounded by a metallic frame 104. In this exemplary embodiment, the substrate 102 comprises polyether ether ketone (PEEK) and is molded into the shape of a wrist plate for use with fractures of the wrist. And the frame 104 is fabricated from stainless steel and cupped about its internal perimeter to retain the substrate therein. In exemplary form, the inner circumferential surface of the metallic frame may be straight, concave, or convex, while the outer circumferential surface of the non-metallic substrate may be straight, concave, or convex.

Specifically, the substrate 102 includes a proximal head portion 106 and a distal shaft portion 108. A top and opposed bottom surface 110, 112 of the substrate 102 are joined by a side or edge surface 114. The proximal head portion 106 is substantially wider than the distal shaft portion 108 and includes a series of through holes 116 extending from the top surface 110 to the bottom surface 112. Likewise, the distal shaft portion includes its own through holes 120.

By way of example, and not limitation, the through holes 116, 120 may be non-threaded and take on a substantially constant circular cross-section along the vertical length of the hole. It should be understood, however, that various shaped through holes 116, 120 may be formed as part of the instant disclosure. For example, the through holes 116, 120 may be threaded. Moreover, the through holes 116, 120 may not include a substantially constant circular cross-section along the vertical length of the hole. An example of a through hole 116, 120 falling within this example would be a bowl-shaped hole where the circular cross-section at the top of the hole (or top surface) is substantially larger that the circular cross-section at the bottom of the hole (or bottom surface). Another example would be through holes 116, 120 have a conical or frustoconical shape. In addition, the through holes need not be circular in vertical cross-section. For instance, the holes 116, 120 may be elongated or comprise a series of overlapping circular holes.

It should also be noted that an axis extending through each hole 116, 120 is not required to be perpendicular to either or both of the top and bottom surfaces 110, 112 of the plate 100. For instance, some of the through holes 116, 120 may be perpendicular with respect to the top or bottom surface 110, 112, while other holes 116, 120 may have axes that are acutely or obtusely angled with respect to the top or bottom surface.

It should be further noted that the holes 116, 120 need not be the same size. Rather certain of the holes 116, 120 may have a circular cross-section with a diameter larger than the diameter of other circular cross-section holes 116, 120. Likewise, some or all of the holes 116 need not have a circular cross-section. Rather, the holes 116, 120 may be elongated in a horizontal direction or take on shapes such as triangular or rectangular. Moreover, some or all of the holes 116, 120 need not have a constant circular cross-section.

By fabricating the substrate 102 from a deformable material such as PEEK, the holes 116, 120 may be slightly deformed by a fastener (e.g., a screw) to provide each fastener in a locked axial orientation that may be different from the original axial orientation of the hole. But the metallic frame 104 ensures that no matter how much the substrate 102 is deformed, the overall outline of the bone plate 100 will be retained.

It should also be noted that if the shape of the overall bone plate needs to be reformed, the metallic frame 104 is deformable to the same or a greater extent than if the entire bone plate had been fabricated from a uniform, metallic substrate.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A composite bone plate comprising:
a rigid frame that defines an internal opening and the outline of a bone plate;
a deformable material mounted to the rigid frame at least partially spanning the internal opening, and including at least one through opening that is concurrently circumscribed by the rigid frame, the at least one through opening defining a first axis for receiving a fastening device, wherein the shape of the at least one through opening is capable of being structurally deformed by the fastening device without structurally deforming the rigid frame such that the fastening device is capable of being lockably threaded to the bone plate at a plurality of different angular orientations off-axis from the first axis; wherein
the deformable material comprises a higher volume percentage of the composite bone plate than does the rigid frame; and
the deformable material comprises a lower weight percentage of the composite bone plate than does the rigid frame.

2. A composite bone plate comprising:
a rigid frame that defines an internal opening and the outline of a bone plate;
a deformable material mounted to the rigid frame at least partially spanning the internal opening, and including at least one through opening that is concurrently circumscribed by the rigid frame, the at least one through opening defining a first axis for receiving a fastening device, wherein the shape of the at least one through opening is capable of being structurally deformed by the fastening device without structurally deforming the rigid frame such that the fastening device is capable of being lockably threaded to the bone plate at a plurality of different angular orientations off-axis from the first axis; wherein
the rigid frame is concave on an inner circumferential surface;
the deformable material is convex on an outer circumferential surface; and
the inner circumferential surface contacts at least a portion of the outer circumferential surface.

3. A composite bone plate comprising:
a rigid frame that defines an internal opening and the outline of a bone plate;
a deformable material mounted to the rigid frame at least partially spanning the internal opening, and including at least one through opening that is concurrently circumscribed by the rigid frame, the at least one through opening defining a first axis for receiving a fastening device, wherein the shape of the at least one through opening is capable of being structurally deformed by the fastening device without structurally deforming the rigid frame such that the fastening device is capable of being lockably threaded to the bone plate at a plurality of different angular orientations off-axis from the first axis; wherein
the deformable material is concave on an outer circumferential surface;
the rigid frame is convex on an inner circumferential surface; and
the inner circumferential surface contacts at least a portion of the outer circumferential surface.

4. A composite bone plate comprising:
a rigid frame that defines an internal opening and the outline of a bone plate; and a deformable material including an outer circumferential surface mounted to the rigid frame by one of a compressed outer circumferential surface and an expanded rigid frame, the deformable material at least partially spanning the internal opening, and including at least one through opening that is concurrently circumscribed by the rigid frame, the at least one through opening defining a first axis for receiving a fastening device, wherein the shape of the at least one through opening is capable of being structurally deformed by the fastening device without structurally deforming the rigid frame such that the fastening device is capable of being lockably threaded to the bone plate at a plurality of different angular orientations off-axis from the first axis, wherein the deformable material includes a plurality of through openings, at least one of the plurality of through openings having a non-uniform circular vertical cross-section.

5. A method of fabricating a bone plate comprising:
fabricating a deformable material into the shape of a bone plate, the deformable material including a plurality of through holes each defining a first axis for receiving a fastening device and each having a shape structurally deformable by the fastening device such that the fastening device is capable of being lockably threaded to the bone plate at a plurality of different angular orientations off-axis from the first axis;
fabricating a rigid frame having an outline that tracks an outline of the deformable material, wherein the rigid frame is not deformable as one or more of the fastening devices is threaded to the bone plate; and
mounting the deformable material to the rigid frame.

6. The method of claim 5, wherein the step of fabricating the deformable material includes shaping the deformable material into the shape of a volar bone plate.

7. The method of claim 5, wherein the deformable material comprises polyether ether ketone.

8. The method of claim 5, wherein the deformable material is fabricated in the shape of a volar bone plate.

9. The method of claim 5, wherein the step of mounting the deformable material to the rigid frame includes at least one of compressing an outer circumferential surface of the deformable material and expanding an inner circumferential surface of the rigid frame.

10. A variable angle bone plate comprising:
a rigid frame; and
a deformable material including an outer circumferential surface mounted to the rigid frame by one of a compressed outer circumferential surface and an expanded rigid frame to create a bone plate, the bone plate having a plurality of holes extending though the deformable material, at least a first of the plurality of holes having a through axis that is not coaxial with a second of the plurality of through holes, wherein the bounds of the plurality of through holes have a shape that is capable of being structurally deformed by a fastening device such that the fastening device is capable of being lockably threaded to the bone plate at a plurality of different angular orientations off-axis from the through axis without deforming the rigid frame.

11. The variable angle bone plate of claim 10, wherein the rigid frame comprises a metal and the deformable material comprises polyether ether ketone.

12. The variable angle bone plate of claim 10, wherein at least one of the plurality of holes has a non-uniform circular vertical cross-section.

13. A variable angle bone plate comprising:
a rigid frame;
a deformable material mounted to the rigid frame to create a bone plate, the bone plate having a plurality of holes extending though the deformable material, at least a first of the plurality of holes having a through axis that is not coaxial with a second of the plurality of through holes, wherein the bounds of the plurality of through holes have a shape that is capable of being structurally deformed by a fastening device such that the fastening device is capable of being lockably threaded to the bone plate at a plurality of different angular orientations off-axis from the through axis without deforming the rigid frame; wherein
the deformable material comprises a higher volume percentage of the variable angle bone plate than does the rigid frame; and
the deformable material comprises a lower weight percentage of the variable angle bone plate than does the rigid frame.

14. A variable angle bone plate comprising:
a rigid frame;
a deformable material mounted to the rigid frame to create a bone plate, the bone plate having a plurality of holes extending though the deformable material, at least a first of the plurality of holes having a through axis that is not coaxial with a second of the plurality of through holes, wherein the bounds of the plurality of through holes have a shape that is capable of being structurally deformed by a fastening device such that the fastening device is capable of being lockably threaded to the bone plate at a plurality of different angular orientations off-axis from the through axis without deforming the rigid frame; wherein
the rigid frame is concave on an inner circumferential surface;
the deformable material is convex on an outer circumferential surface; and
the inner circumferential surface contacts at least a portion of the outer circumferential surface.

15. A variable angle bone plate comprising:
a rigid frame;
a deformable material mounted to the rigid frame to create a bone plate, the bone plate having a plurality of holes extending though the deformable material, at least a first of the plurality of holes having a through axis that is not coaxial with a second of the plurality of through holes, wherein the bounds of the plurality of through holes have a shape that is capable of being structurally deformed by a fastening device such that the fastening device is capable of being lockably threaded to the bone plate at a plurality of different angular orientations off-axis from the through axis without deforming the rigid frame; wherein
the deformable material is concave on an outer circumferential surface;
the rigid frame is convex on an inner circumferential surface; and
the inner circumferential surface contacts at least a portion of the outer circumferential surface.

* * * * *